United States Patent [19]

Katakura et al.

[11] Patent Number: 4,974,558
[45] Date of Patent: Dec. 4, 1990

[54] ULTRASONODIAGNOSTIC TOMOGRAPHY APPARATUS

[75] Inventors: Kageyoshi Katakura; Toshio Ogawa, both of Tokyo; Shinichiro Umemura, Hachioji; Sizuo Ishikawa, Kanagawa, all of Japan

[73] Assignee: Hitachi Medical Corporation, Tokyo, Japan

[21] Appl. No.: 769,805

[22] Filed: Aug. 27, 1985

Related U.S. Application Data

[63] Continuation of Ser. No. 463,652, Feb. 3, 1983, abandoned.

[30] Foreign Application Priority Data

Feb. 3, 1982 [JP] Japan .................................. 57-14867

[51] Int. Cl.⁵ .............................................. A61B 8/14
[52] U.S. Cl. .................................. 128/661.01; 73/626
[58] Field of Search ........................... 128/660, 661.01; 73/625, 626

[56] References Cited

U.S. PATENT DOCUMENTS

| 4,145,931 | 3/1979 | Tancrell | 128/660 |
| 4,235,111 | 11/1980 | Hassler | 73/626 |
| 4,254,662 | 3/1981 | Kuroda et al. | 128/660 |
| 4,307,613 | 12/1981 | Fox | 128/660 |
| 4,368,643 | 1/1983 | Tachita et al. | 128/660 |

FOREIGN PATENT DOCUMENTS 0017383 10/1980 European Pat. Off. ............ 128/660

Primary Examiner—Ruth S. Smith
Attorney, Agent, or Firm—Antonelli, Terry, Stout & Kraus

[57] ABSTRACT

In an ultrasonodiagnostic tomography apparatus for transmitting focused sound wave from a plurality of transducers forming an array to a predetermined focus point and for carrying out beam formation for receiving sound from said focus point with dynamic focusing, wherein the width of transmission beam at said focus point is controlled by means of said transducers so that the width of transmission beam at said focus point may be larger than the width of receiving beam from said focus point.

2 Claims, 7 Drawing Sheets

AMPLITUDE   PHASE

ARRAY ELEMENT NO.

ARRAY ELEMENT NO.

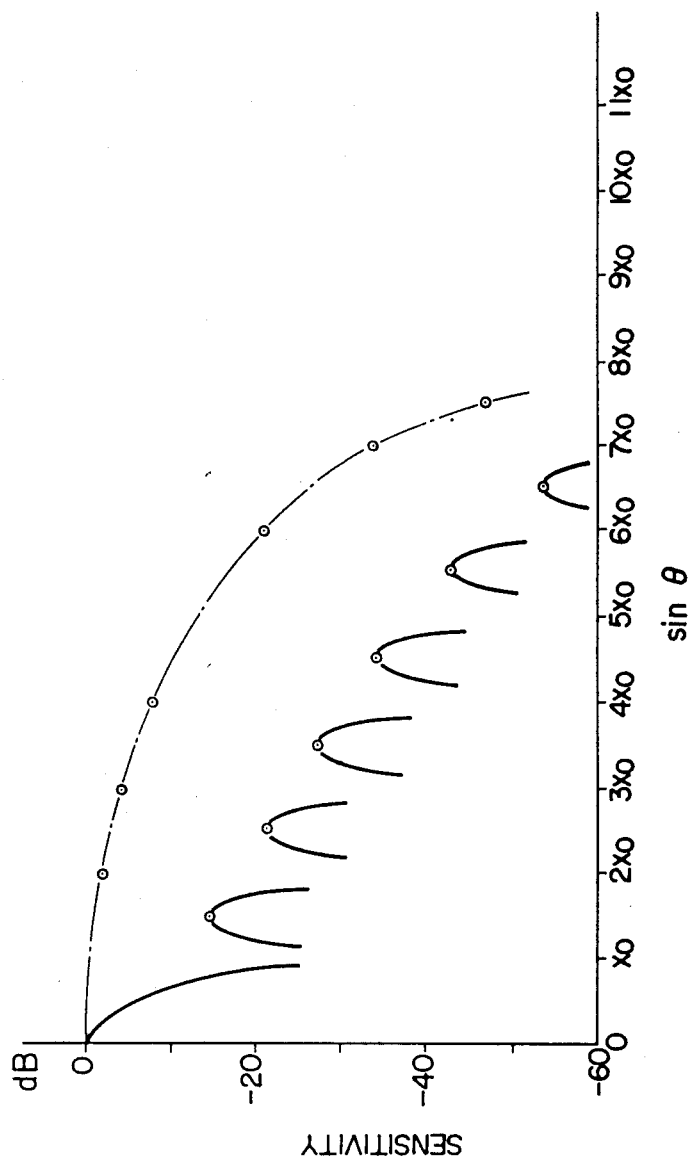

DEPTH r

TIME

ULTRASONODIAGNOSTIC TOMOGRAPHY APPARATUS

This application is a continuation, of application Ser. No. 463,652, filed Mar. 27, 1983 now abandoned.

BACKGROUND OF THE INVENTION

1. Field of the Invention

The present invention relates to an ultrasonodiagnostic tomography apparatus and in particular to an electronic scanned ultrasonodiagnostic tomography apparatus.

2. Description of the Prior Art

In a prior art ultrasonodiagnostic apparatus for viewing an object to be inspected or specimen on the basis of a reflected echo of an ultrasound beam applied into the object, the number of transducers in the array transducer is selected by switching means and the aperture of transmitter is determined to be approximately equal with that of receiver. The prior art system is hereinafter referred to as the system having equal apertures for transmitter and receiver.

If the apertures of transmission and receiving are made larger in order to get higher resolution, the number of elements is increased because of the necessity for a nearly constant pitch of the array elements. This results in the drawback that it becomes impossible to realize the switching means.

On the other hand, if the element pitch is increased while holding the number of elements constant, the level of undesired sound signals is raised, resulting in the deterioration of image quality.

For obtaining favorable resolutions in all depth directions in the prior art system having equal apertures for transmission and receiving, it becomes necessary to use the so-called "multistage focusing (dynamic focusing)" wherein transmission is effected plural times while changing the transmission focus. When it is contrived to get higher resolution in this prior art system, the focal depth is rapidly decreased, and hence the number of stages is largely increased, the frame rate being largely lowered.

SUMMARY OF THE INVENTION

In view of the above-described fact, the object of the present invention is to provide an apparatus for obtaining an ultrasonodiagnostic tomography image having high resolution in all depth directions of an object to be inspected without lowering the frame rate.

In order to achieve this object, according to an aspect of the present invention, an ultrasound is transmitted with a small aperture to be focused at one point (fixed focus) at the time of transmission and the transmitted ultrasound is subjected to dynamic focusing with a large aperture at the time of receiving.

BRIEF DESCRIPTION OF THE DRAWINGS

FIG. 4 and FIG. 5 are drawings for illustrating the characteristics of the ultrasound beam according to the present invention.

DESCRIPTION OF THE PREFERRED EMBODIMENTS

Figure 1:
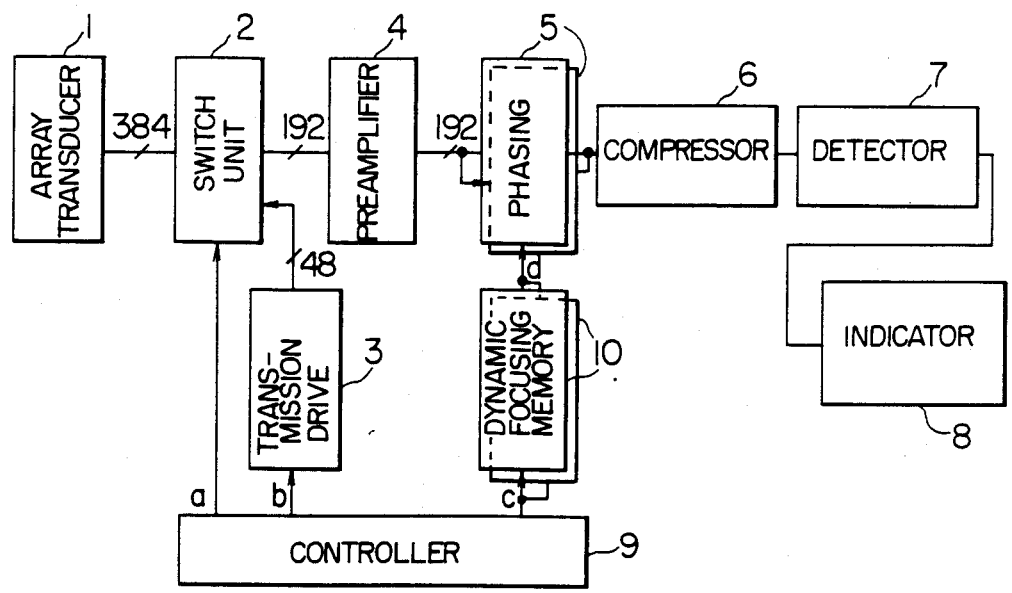
FIG. 1 is a block diagram for illustrating the constitution of an embodiment of the present invention.

FIG. 1 is a block diagram for illustrating the constitution of an embodiment of the present invention. In FIG. 1, numeral 1 denotes an array transducer composed of, say, 384 elements, numeral 2 denotes a switch unit over transmission and receiving, numeral 3 denotes a driver circuit for transmission, numeral 4 denotes a preamplifier, numeral 5 denotes a phasing-network (delay-line beam-former) for receiving, numeral 6 denotes a compressor circuit, numeral 7 denotes a detector circuit, numeral 8 denotes a display, numeral 9 denotes a controller, numeral 10 denotes a dynamic focusing memory for receiving, and marks a, b and c denote control output signals from the controller 9 respectively for the switch unit 2, driver circuit 3, and the dynamic focusing memory 10 for receiving. Mark d denotes the output of the dynamic focusing memory 10 for controlling the phasing-network 5. In the memory 10, delay values to be fed to the phasing-network 5 for forming a focus point for each depth are stored. In this constitution, the aperture of transmission (48 elements, for example) and the aperture of receiving (192 elements, for example) are selected out of all of 384 elements in the array transducer 1 by the switch unit 2 according to the control signal a of the controller 9. The amplitude and phase in the driver circuit 3 are controlled by the control signal b of the controller 9 to drive the array transducer 1 via the switch unit 2. The dynamic focusing memory 10 for receiving is controlled by the control signal c from the controller 9. Each of the signals received by 192 elements is amplified by the preamplifier 4. Thereafter, in the phasing-network 5 for receiving, the signals for respective depths are subjected to phase alignment and added to yield the output by the data d from the dynamic focusing memory 10. Thereafter, the reflected ultrasound signal passed through the compressor circuit 6 and the detector circuit 7 is indicated on one scan line of the indicator 8. Then, the aperture of transmission and receiving is successively moved by the control signal a from the controller 9 to display the ultrasonodiagnostic tomography image on the indicator 8.

Figure 2A:
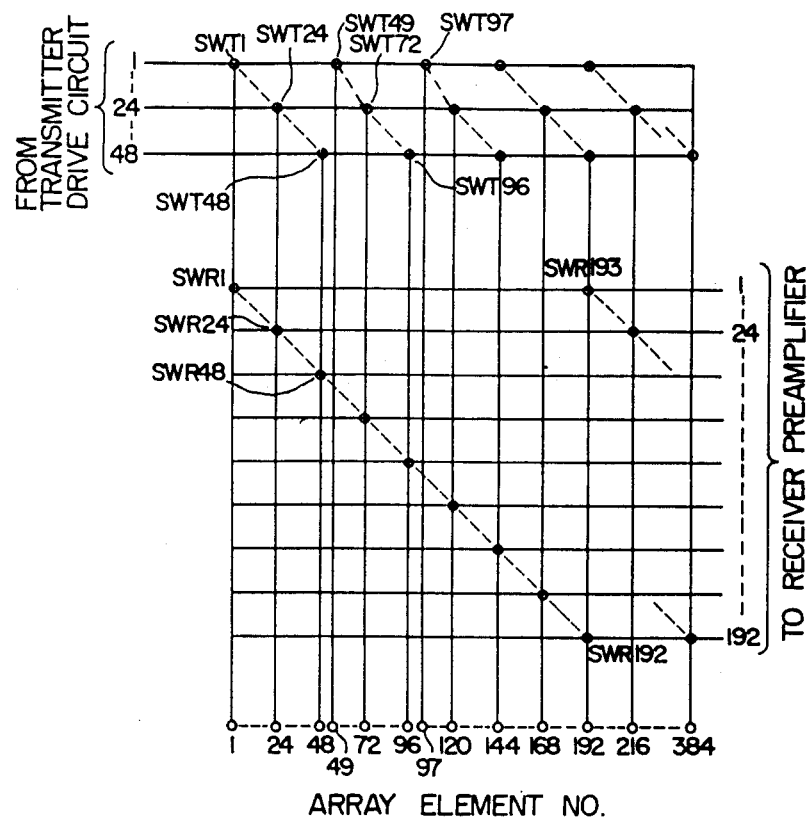
FIG. 2a is a drawing for illustrating the operation of the embodiment as shown in FIG. 1.
Figure 2B:
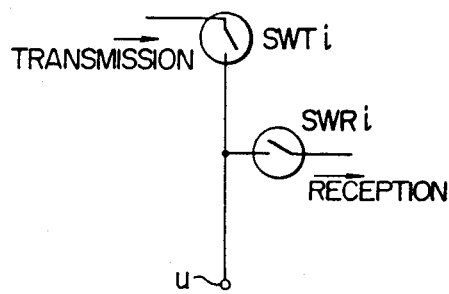
FIG. 2b is a drawing for illustrating the principal part of the embodiment as shown in FIG. 1.

The constitution and operation of the switch unit 2 shown in FIG. 1 will be hereafter described referring to FIG. 2a and FIG. 2b. In FIG. 2a, channel 1 in the 48-channel transmitter drive circuits is connected to array elements #1, #49, #97, #145 and so on via transmitter switches SWTi (i=1, 49, 97, 145 and so on). In the same way, channel 24 of the transmitter drive circuit is connected to array elements #24, #72, #120 and so on, and channel 48 is connected to array elements #48, #96, #144 and so on. On the other hand, array elements are connected to 192-channel preamplifiers via receiver switches SWRi. The transmitter switch SWTi and the receiver SWRi are both connected with the array element u as shown in FIG. 2b. As shown in FIG. 2a, the transmitter switch SWTi is placed on the intersection of each drive circuit and each array element u. As shown in FIG. 2b, the receiver switch SWRi is placed on the intersection of each array element u and each receiver preamplifier. Control signals for switches SWTi and SWRi which correspond to the control signal a shown in FIG. 1 are omitted in FIG. 2a and FIG. 2b.

At first in this constitution, only the transmitter switches SWT1 to SWT48 and only the receiver switches SWR1 to SWR192 are turned ON to transmit ultrasounds by means of array elements #1 to #48 and to connect received signals on array elements #1 to #192 to preamplifiers. Subsequently, only the transmission switches SWT2 to SWT49 and only the receiving switches SWR2 to SWR193 are turned ON to transmit ultrasounds by means of array elements #2 to #49 and also to connect received signals on array elements #2 to #193 to the preamplifiers.

As the control signal generator for the switches SWTi, a 384-bit ring counter, for example, is employed. Only 48 bits in the ring counter are in the "1" state and the remaining bits are in the "0" state. The switches SWTi turn ON for the control signal "1" and turn OFF for the control signal "0". The same method is also applied to the switches SWRi. In this way, it becomes possible to move the aperture of transmission and receiving owing to the constitution of switch unit as shown in FIG. 2a and FIG. 2b.

Figure 3A:
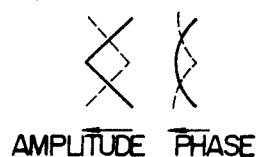
FIGS. 3a and 3b are another drawings for illustrating the operation of the embodiment as shown in FIG. 1.
Figure 3B:
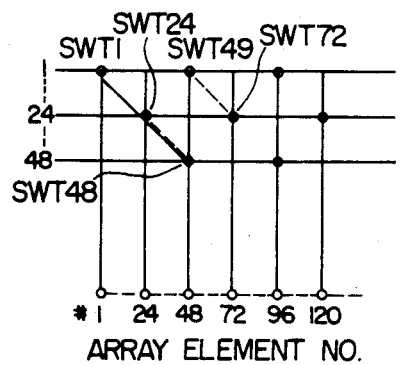

When the aperture is changed by means of the switch unit 2, the correspondence between the input/output terminal number of transmission or receiving and the aperture position of transmission or receiving is also changed. Adjustment of amplitude or phase data thus required will be hereafter described referring to FIGS. 3a and 3b.

At first, the adjustment for transmission will be described. It is now assumed that the transmission beam is focused by providing the aperture of transmission with the triangularly tapered amplitude distribution and concave phase distribution. In the triangular tapered or weighted amplitude distribution, the elements placed at the center of the aperture are driven with the largest amplitude, the elements placed at both ends of the aperture are driven with zero amplitude, and the intermediate elements are driven with the amplitude varying linearly. On the other hand, in the usual rectangular weighted amplitude distribution, all of the array elements are driven with equal amplitude.

Supposing that the aperture of transmission moves form the solid line (#1 to #48) to the broken line (#24 to #72) as shown in FIG. 3, it is necessary to vary the outputs 1 to 48 of transmission drive circuit from the solid line shown in FIG. 3 to the broken lines in the figure. This is accomplished by controlling the driver circuit 3 shown in FIG. 1 by means of the control signal b from the controller 9.

In the above, the adjustment for transmission has been described. Also for receiving, the adjustment is accomplished as a result of control of the dynamic focusing memory 10 for receiving by means of the control signal c in the same way as the transmission.

FIG. 4 illustrates characteristic curves of the transmission and receiving beam for the present invention wherein the abscissa represents $\sin\theta$, where $\theta$ is a deflection angle, and the ordinate represents the normalized transmission or receiving sensitivity. The solid line shows the case where the aperture of transmission is 16 mm and the aperture of receiving is 64 mm. The broken line represents the width of the ultrasound beam near the focus points in the system having equal apertures of 32 mm for transmission and receiving. The dotted chain line represents the transmission beam characteristics near the focus points.

In this way, the width of the received beam (zero point) near the transmission focus point becomes $\frac{1}{8}$ as compared with that of the transmission beam according to the present invention. Accordingly, the main beam of transmission and receiving beam illustrated by the solid line in FIG. 4 nearly coincides with the received beam. In addition, owing to the wide width of transmission beam, it is possible to obtain a plurality of received beams by displacing the direction of the received beam from that of the transmitted beam by a slight amount, for example $\pm 2X_o$ where $X_o = \lambda/D$, $\lambda$ is the wavelength and D is the aperture of receiving. For obtaining a plurality of received beams, the phasing-network 5 and the receiving memory 10 must be provided in multiple plurality as illustrated in FIG. 1. Accordingly, the size of hardware is increased. However, the advantage of a large frame rate is obtained.

Figure 5:
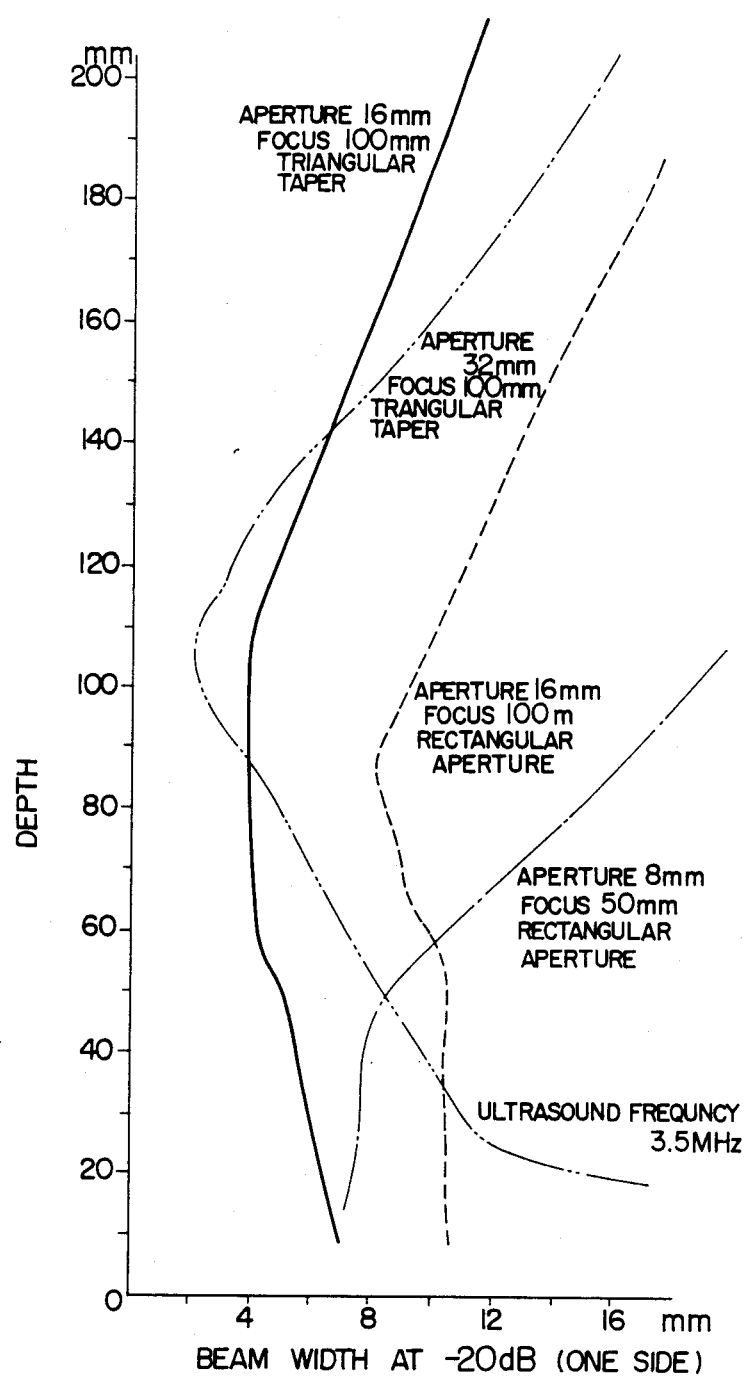

The ultrasound beam near the transmission focus point has heretofore been described. FIG. 5 shows the characteristics of the transmission beam at various depths. In FIG. 5, the solid line shows the case where the aperture of transmission is 16 mm, the focus point is 100 mm and the weighting is triangularly tapered. The broken line in FIG. 5 shows the case where the weighting is rectangular and the remaining conditions are the same as those of the solid line. The dotted chain line shows the case where the aperture of transmission is 8 mm, the focus point is 50 mm, the weighting is rectangular, and the beam width (one side) is a value at $-20$ dB. The two dotted chain line shows the case where the aperture of transmission is 32 mm, the focus point is 100 mm, and the weighting is triangularly tapered.

In this way, it is possible to obtain nearly uniform transmission beams in all areas in the depth direction by adopting the aperture of 16 mm and the triangular weighting. Even if the aperture is decreased to a half, i.e., 8 mm while maintaining the rectangular weighting, the directional performance is not improved as shown in FIG. 5. On the contrary, if the aperture of transmission is further increased to 32 mm, the beam at positions other than the focus point is largely deteriorated.

As heretofore described, according to the present invention, it becomes possible to obtain the transmitter beam which is uniform in the depth direction and relatively wide by adopting a small aperture of transmission and amplitude weighting, to obtain a plurality of narrow receiving beams by adopting a large aperture of receiving, and to obtain in real time the transmission and receiving beam which is highly resolvable in all depths by adopting the dynamic focus.

In the above description, it has been assumed that the aperture of receiving has rectangular weighting. If the aperture of receiving has triangular weighting, the width of the main beam is doubled. However, this results in the advantage that the undesired sound signal level is suppressed. In the above description, it has also been assumed that the amplitude weighting is triangularly tapered. However, it is a matter of course that the Hanning weighting, Hamming weighting or the like may be used.

In the above description, beam reception with a large aperture has been explained. The present invention is not limited to this case and it is also possible to obtain the entire aperture of receiving by successively synthesizing apertures of receiving. That is to say, the entire aperture of receiving is synthesized by partially receiving the beam and aligning its phase each time transmission is effected. The principle in this case will be hereafter described referring to FIG. 6.

Figure 6:
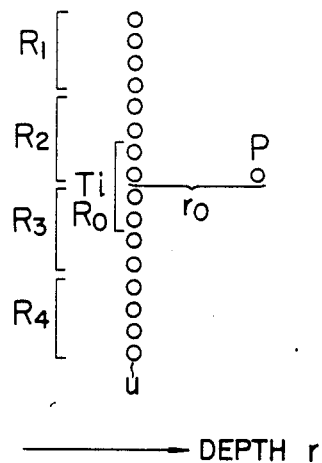
FIG. 6 is a drawing for illustrating the principle of the present invention.
Figure 7:
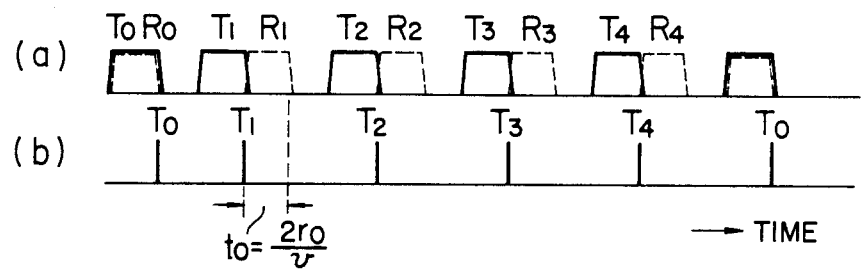
FIG. 7 is a time chart for illustrating the operation in FIG. 6.

In FIG. 6, Ti (i=0,1, 2, 3, 4) denotes the aperture of transmission, $R_o$ denotes the aperture of short distance receiving, $R_1$, $R_2$, $R_3$ and $R_4$ denotes partial apertures of long distance receiving, and $R_1+R_2+R_3+R_4$ denote the entire aperture of long distance receiving. In addition, r represents the distance in the depth direction and $r_o$ represents the distance between the particular point P and the transducer. FIG. 7 is a time chart for explaining the operation in FIG. 6. FIG. 7(a) shows the control voltage waveform for the changeover switch of the array transducer u. Ti and Ri (i=0, 1, 2, 3, 4) in FIG. 7(a) correspond to those in FIG. 6. FIG. 7(b) shows a time chart of transmitter pulses. In FIG. 7(b), $r_o$ denotes the distance between the array transducer and the particular point p and v denotes the sound velocity.

As represented by $T_o$ and $R_o$ in FIG. 7(a), equal apertures for transmitter and receiver are selected by means of the changeover switches. As represented by $T_o$ in FIG. 7(b), transmission ($T_o$) is effected and immediately after that reception is effected at the same position ($R_o$). Succeedingly, the aperture of transmission is selected as represented by $T_1$ in FIG. 7(a) which is the same position as $T_o$. As represented by $T_1$ in FIG. 7(b), transmission is effected. Immediately after that, the partial aperture of receiving is selected as represented by $R_1$ in FIG. 7(a). After the period $$t_o = \frac{2r_o}{v}$$

has elapsed, phasing or phase alignment are effected with the partial aperture $R_1$ of receiver. Succeedingly, the aperture of transmission is selected as represented by $T_2$ in FIG. 7(a) and transmission is effected as represented by $T_2$ in FIG. 7(b). Immediately after that, the partial aperture of receiving is selected as represented by $R_2$ in FIG. 7(a). When the period $t_o$ has elapsed after that, reception and phase alignment are effected with the partial aperture $R_2$ of receiving.

The same procedure is repeated after that. When $T_4$ and $R_4$ have been finished, the received signals for the entire aperture are subjected to phase alignment.

The period $t_o$ is the time required for the diode switch controlled with high voltage in the switch unit to be on-off controlled, and $r_o$ is approximately 30 mm.

In addition, it is evident that the result obtained by adding the phase aligned outputs of partial apertures $R_1$, $R_2$, $R_3$ and $R_4$ of receiving while holding their phases is equivalent to the phase aligned output of the entire aperture of receiving.

In the above description, the aperture of receiving is quartered to form partial apertures of receiving. It is a matter of course that other division may be adopted.

Figure 8:
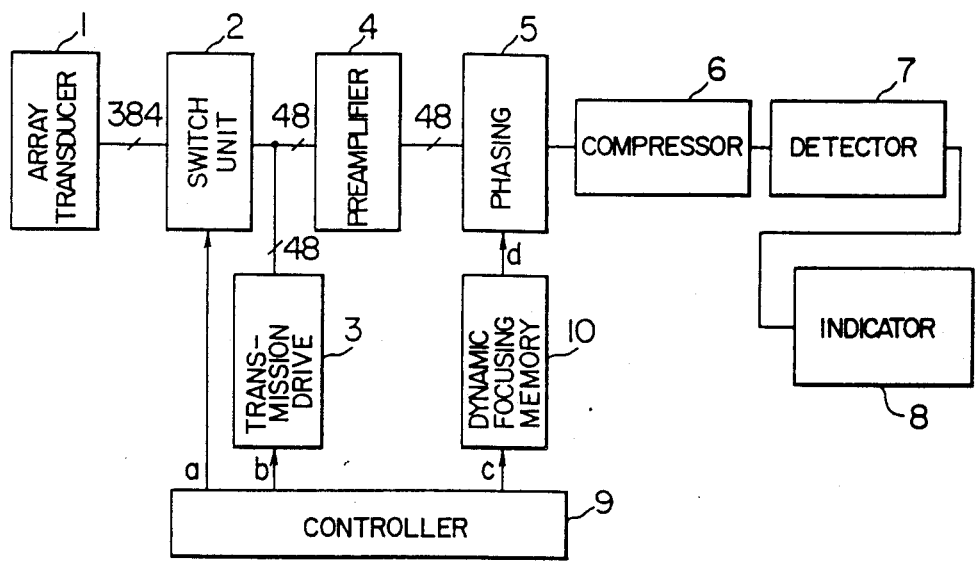
FIG. 8 is a block diagram for illustrating the constitution of another embodiment of the present invention.
Figure 9:
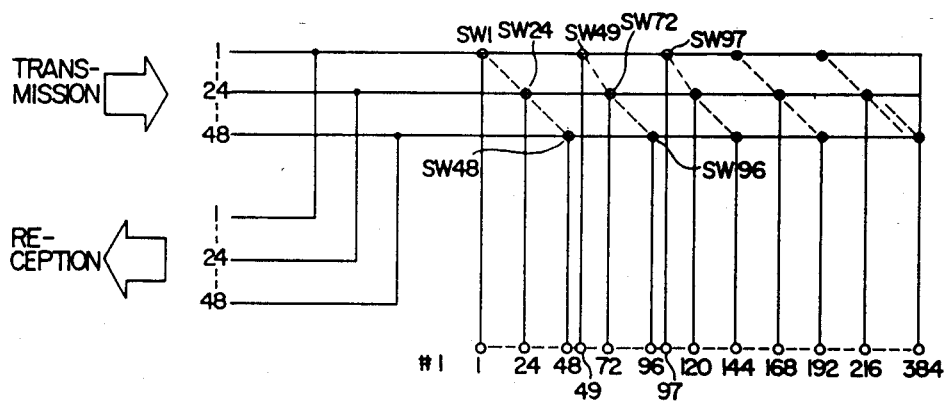
FIG. 9 and FIG. 10 are drawings for illustrating the principal part of the embodiment as shown in FIG. 8.

FIG. 8 is a block diagram for illustrating the constitution of an embodiment of the present invention wherein the principle illustrated in FIG. 6 is realized. The constitution of FIG. 8 is the same as that of FIG. 1. However, the switch unit for transmitter and receiver 2 is controlled as illustrated in FIG. 9. In addition, the number of outputs from the switch unit 2 is reduced to a quarter as compared with that in FIG. 1.

In such constitution, the aperture of transmission (48 elements) and the partial aperture of receiving (48 elements) are selected out of all of 384 elements in the array transducer 1 by the switch unit 2 according to the control signal a from the controller 9. In the transmitter drive circuit 3, the amplitude and phase of each of 48 elements for forming the aperture of transmitter are controlled by the control signal from the controller 9. The array transducer 1 is driven by the transmission drive circuit 3 via the switch unit 2. On the other hand, each of the signals received by 48 elements for the partial aperture of receiving is amplified by the preamplifier 4. Thereafter, in the phasing-network 5 for receiving, the signals are subjected to phase alignment and addition under control of the output d from the dynamic focus memory 10 which is controlled by the control signal c from the controller 9.

As a result, the output of the phasing-network 5 for receiving is obtained and the output corresponds to the partial aperture $R_1$ illustrated in FIG. 6.

Subsequently, transmission is effected with the same aperture for transmission. In the same way, reception is successively effected with the partial apertures $R_2$, $R_3$ and $R_4$. And the phase-aligned and added output for the entire aperture is sent out from the phasing-network 5 for receiving.

Thereafter, the reflected ultrasound signal passed through the compressor circuit 6 and the detector circuit 7 is displayed on one scan line of the indicator 8. In addition, the aperture of transmission and receiving is successively moved by the control signal a from the controller 9 to display the ultrasonodiagnostic tomography image on the indicator 8.

The constitution of the switch unit 2 illustrated in FIG. 8 will be hereafter described referring to FIG. 9.

The 48-channel input ends of the transmission drive circuit are respectively connected to output ends for the 48-channel received signals.

Channel 1 of the transmission drive circuit and preamplifier for received signals is connected to array elements #1, #49, #97 and so on via SWi (i=1, 49, 97, and so on). Channel 48 is connected to array elements #48, #96, #144 and so on via SWi (i=48, 96, 144 and so on). The control signal for each switch SWi which corresponds to the control signal a shown in FIG. 8 is omitted in FIG. 9.

As shown in FIG. 2, FIG. 3 and FIG. 6, at first the aperture Ti for transmission is selected by the switch SWi to effect transmission. Immediately after the transmission, the aperture Ri for transmission is selected by the switch SWi to obtain the received signal. The sequence of control signals for switches is previously stored in the read only memory (ROM) which is contained in the control circuit 9.

Figure 10:
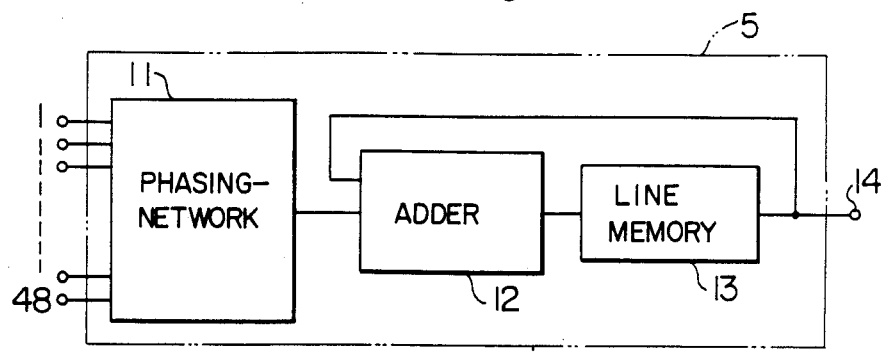

Phase alignment for the received signal of the partial aperture which has been obtained by using the switch unit shown in FIG. 9 will be hereafter described referring to FIG. 10.

FIG. 10 shows details of an embodiment of the phasing-network 5 shown in FIG. 8.

In FIG. 10, numerals 1 to 48 denote input terminals for received signals shown in FIG. 9. That is to say, numerals 1 to 48 are input terminals to the phasing-network 5 shown in FIG. 8. Numeral 11 denotes a phasing-network for 48-channel received signals. Numeral 13 denotes a line memory. Numeral 12 denotes an adder having one input coupled to the output of the above described phasing-network 11 and the other input coupled to the output of the line memory 13. And numeral 14 denotes an output terminal of the phasing-network 5 shown in FIG. 8.

In such constitution, 48-channel received signals for the partial aperture $R_1$ are subjected to phase alignment and addition in the phasing-network 11 and held in the line memory 13 via the adder 12. Subsequently, the received signals for the partial aperture $R_2$ is subjected to phase alignment and addition and thereafter added to the received signals for the partial aperture $R_1$ coherently in the adder 12. Thereafter, in the similar procedures, the received signals for the partial aperture $R_3$ and $R_4$ are added. After transmission has been effected four times, receiving and phase alignment for the entire aperture are conducted to yield the output at the output terminal 14.

In this way, it becomes possible to obtain the entire aperture for receiving by synthesizing the partial apertures for receiving. Therefore, it is possible to simplify the phasing-network for receiving and the switch unit.

Figure 11:
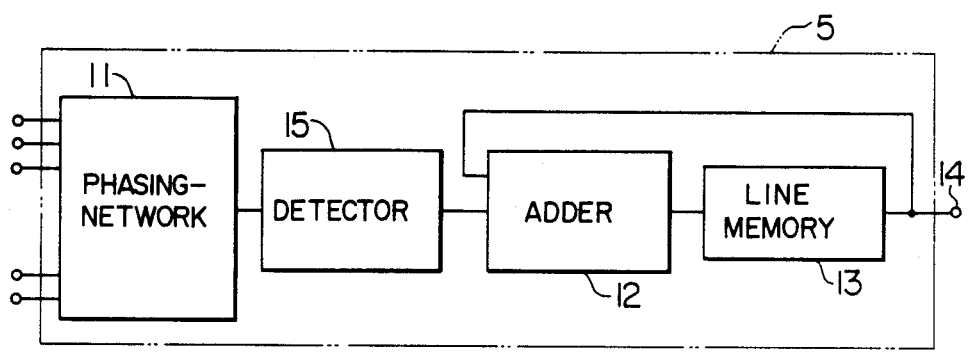
FIG. 11 is a drawing for illustrating the constitution of the principal part of still another embodiment of the present invention.

For obtaining one scan line in synthesizing the partial apertures for receiving, however, transmission and reception are repeated a plurality of times to effect the coherent addition. Accordingly, especially when the object moves fast, the signal might be weakened due to phase cancellation between the received signals. In such a case, it is possible to prevent such a problem by passing the phase aligned outputs of respective partial apertures through a detector 15 prior to addition as shown in FIG. 11. The constitution shown in FIG. 11 is the same as that of FIG. 10 excepting the detector 15. By means of the so-called incoherent addition, the above described problem is prevented to occur.

As described above, the present invention brings about the advantage of a faster frame rate because a plurality of received beams can be obtained in real time for a single transmission owing to the fact that the beam width for receiver is narrower compared to that for transmitter. A large aperture for receiver usually results in the large equipment size. However, it is possible to obtain a reasonable equipment size by receiving a beam with a part of aperture used for transmission each time transmission is effected and obtaining received beams for the entire aperture after the same beam has been transmitted a plurality of times (successive synthesis for receiver).

We claim:

1. An ultrasonodiagnostic tomography apparatus comprising:

a transducer array having a plurality of transducer elements, transmission drive means for providing drive signals so as to form a transmission beam, receiving means for receiving signals from said transducer elements and for phasing and adding the received signals to simultaneously form a plurality of focussed receiving beams which are displaced from one another in a direction transverse to the transmission beam direction and having respective focus points, switch means connected with said transducer array, said transmission drive means and said receiving means for selectively connecting selected ones of said transducer elements to said transmission drive means and said receiving means, memory means for storing delay values to be fed to said receiving means, control means connected with said switch means, said transmission drive means and said memory means for controlling said switch means to form a receiving aperture composed of selected ones of said transducer elements larger than a transmitting aperture, said control means controlling said memory means to apply said delay values therefrom onto said received signals for shifting said focus points.

2. An ultrasonodiagnostic tomography apparatus comprising:

a transducer array having a plurality of transducer elements, transmission drive means for providing drive signals so as to form a transmission beam, receiving means for receiving signals from said transducer elements and for phasing and adding the received signals to form a receiving beam signal representing a focused receiving beam, switch means connected with said transducer array, said transmission drive means and said receiving means for selectively connecting selected ones of said transducer elements to said transmission drive means and said receiving means, memory means for storing delay values to be fed to said receiving means, and control means connected with said switch means said transmission drive means and said memory means for controlling said switch means to form a transmitting aperture composed of selected ones of said transducer elements a plurality of times and to form different partial receiving apertures composed of selected ones of said transducer elements after each time of transmission, said partial receiving apertures forming a whole receiving aperture larger than said transmitting aperture, said control means controlling said memory means to apply said delay values therefrom onto receiving means for forming a focus point of said receiving beam and for shifting said focus point in a depth direction.

* * * * *